United States Patent [19]
Hakky

[11] Patent Number: 5,201,731
[45] Date of Patent: Apr. 13, 1993

[54] LASER RESECTOSCOPE WITH ULTRASONIC IMAGING MEANS

[76] Inventor: Said I. Hakky, 8547 Merrimoor Blvd. East, Largo, Fla. 34647-3145

[21] Appl. No.: 721,032

[22] Filed: Jun. 26, 1991

Related U.S. Application Data

[60] Continuation of Ser. No. 540,072, Jun. 19, 1990, Pat. No. 5,061,266, which is a division of Ser. No. 175,014, Mar. 30, 1988, Pat. No. 4,955,882.

[51] Int. Cl.$^5$ .............................................. A61B 17/36
[52] U.S. Cl. ................................... 606/15; 128/662.05
[58] Field of Search ............................. 128/6, 395-398, 128/660.03, 660.07, 661.03, 662.06; 604/20, 22; 606/2, 13-16, 167, 170, 180

[56] References Cited

U.S. PATENT DOCUMENTS

| | | |
|---|---|---|
| 3,732,858 | 5/1973 | Banko . |
| 3,858,577 | 1/1975 | Bass et al. ............................. 606/15 |
| 3,906,954 | 9/1975 | Baehr et al. . |
| 4,185,633 | 1/1980 | Prozorov et al. . |
| 4,249,533 | 2/1981 | Komiya . |
| 4,266,547 | 5/1981 | Komiya . |
| 4,273,127 | 6/1981 | Auth et al. . |
| 4,556,057 | 12/1985 | Hiruma et al. ......................... 606/14 |
| 4,572,201 | 2/1986 | Kondo et al. ................... 128/662.05 |
| 4,576,177 | 3/1986 | Webster . |
| 4,620,547 | 11/1986 | Boebel . |
| 4,627,435 | 12/1986 | Hoskin . |
| 4,641,650 | 2/1987 | Mok ..................................... 128/665 |
| 4,694,828 | 9/1987 | Eichenbaum . |
| 4,742,829 | 5/1988 | Law et al. ...................... 128/662.06 |
| 4,785,806 | 11/1988 | Deckelbaum ........................ 606/15 |
| 4,791,926 | 12/1988 | Fry . |

FOREIGN PATENT DOCUMENTS 2044104 10/1980 United Kingdom .

Primary Examiner—Max Hindenburg
Attorney, Agent, or Firm—Caesar, Rivise, Bernstein, Cohen & Pokotilow, Ltd.

[57] ABSTRACT

A resectoscope for prostate surgery is provided which includes a rotating cutting element mounted within an outer sheath adapted to be inserted into the urethra. The cutting element has helical threads along the length thereof and a cutting blade at its distal end. The outer sheath has a covered distal end portion which extends beyond and over the cutting blade and has an opening therethrough adjacent the cutting blade. Within the outer sheath is an inner sheath surrounding the cutting element except for the cutting blade. A fiber optic laser filament connected to a laser generator is positioned within the space between the inner and outer sheaths and extends along the length of the inner sheath to a position adjacent the cutting blade. The optic filament is surrounded by a third sheath and is adapted to be moved by the rotation of the cutting element so that the laser light beam from the optic filament advances through tissue to cut and coagulate the resected area before the cutting blade of the cutting element reaches the resected tissue. Irrigation fluid is provided to the area between the inner and outer sheaths and is withdrawn through the inner sheath. A telescope is also provided through the cutting element for viewing the area being resected. The invention further provides for the use of ultrasound in conjunction with the laser resectoscope to plot the area of the prostate to be removed and with the assistance of a computer to control the operation of the laser to prevent cutting of tissue beyond the area of tissues to be removed.

18 Claims, 4 Drawing Sheets

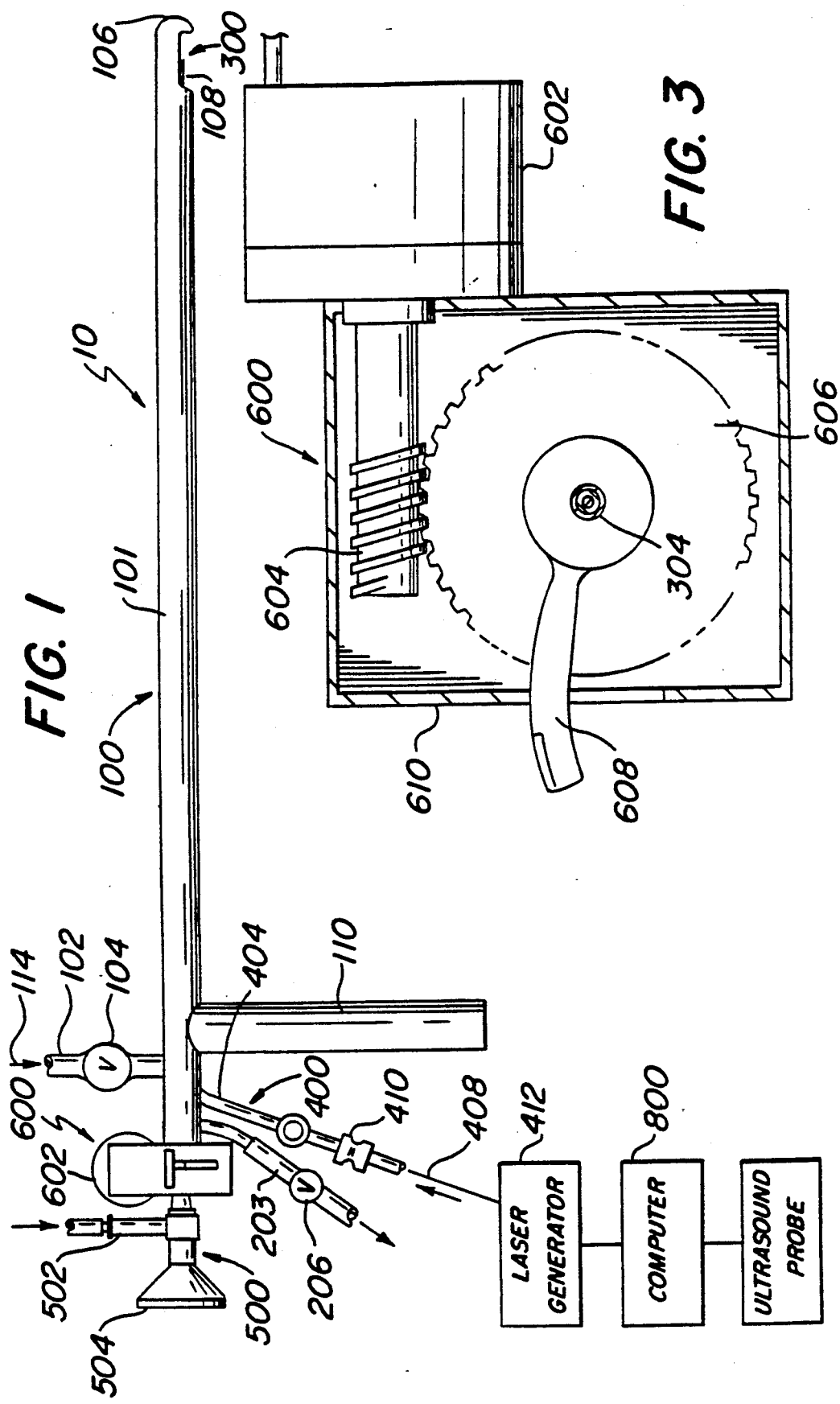

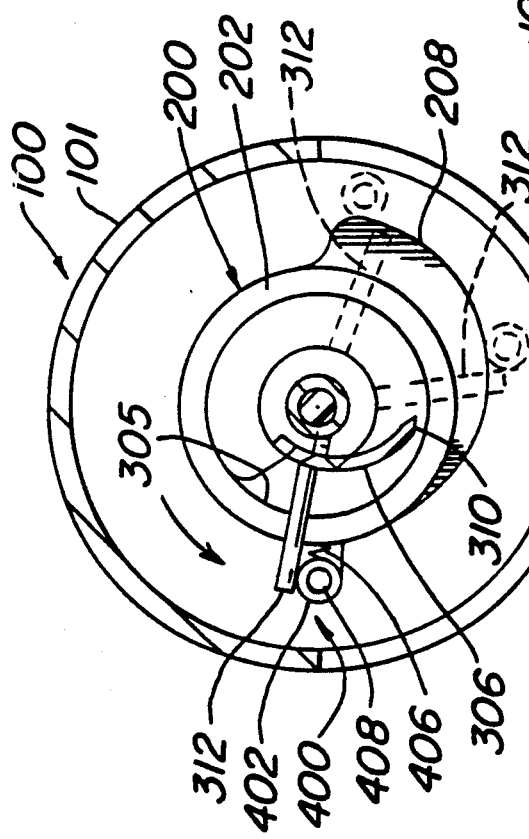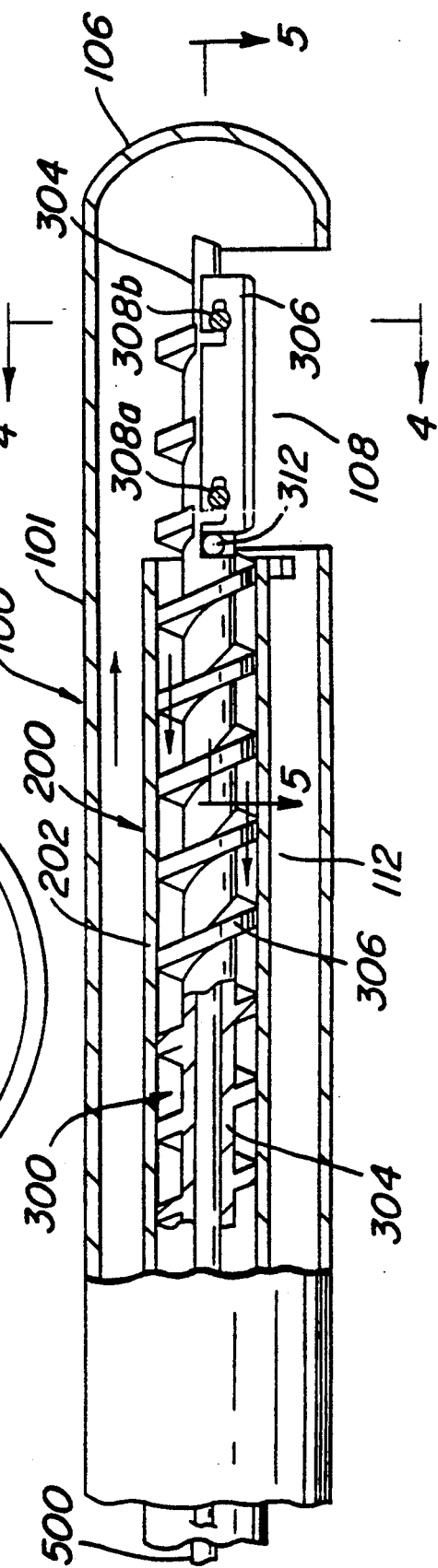

LASER RESECTOSCOPE WITH ULTRANSONIC IMAGING MEANS

This application is a continuation application of application Ser. No. 540,072, filed Jun. 19, 1990 now U.S. Pat. No. 5,061,266 which is a divisional application of application Ser. No. 07/175,014 filed Mar. 30, 1988, now U.S. Pat. No. 4,955,882.

BACKGROUND ART

This invention relates generally to the field of surgical devices, and more specifically to a resectoscope.

A resectoscope is employed transurethrally to perform prostate and/or bladder surgery. This device has an elongate central working section provided with an outer sheath, usually made of stainless steel, which is inserted into the urethra. The outer sheath prevents the urethra from collapsing, while the working elements internally of the sheath are employed to cut away the desired tissue.

Conventional resectoscopes either are of the cold punch type, wherein the cutting element is unheated, or are of the heated type, where a cutting element, in the form of a conductive wire, is heated through an electrical connection to a diathermy unit. The diathermy unit can be controlled by the surgeon, either through the use of a hand-operated switch or through the use of a foot-operated switch.

In a manually operated resectoscope of the type employing a heated cutting element, the surgeon manually extends the cutting element beyond the end of the outer sheath to a position engaging the tissue to be cut. Thereafter, the cutting element is energized through actuation of the diathermy unit, and at the same time the cutting element is manually retracted to cause it to slice away a desired amount of the tissue. The surgeon views the area being operated upon through a telescopic system that also is mounted within the stainless steel sheath of the device, and a continuous irrigation system is utilized to keep the line-of-sight free of blood and other debris.

During prostate surgery it is common to cut away approximately 1/10 of a gram of tissue with each cutting stroke of the resectoscope. Although the total weight of tissue to be removed varies with the size of the individual and the severity of the problem, it is quite common to remove anywhere from 20 to 150 grams of tissue in a typical prostate operation. Therefore, in even the simplest of operations, it is generally necessary to reciprocate the cutting element at least 200 times.

During transurethral resection of the prostate, fluids are used to irrigate during the operation as well as during the immediate postoperative period. The fluid irrigation during the resection has two purposes: to first clarify the area so that the operator's vision is unobstructed and second to remove any prostatic chips toward the bladder. Therefore, the bladder acts as a temporary reservoir for prostatic chips and blood clots. Before the procedure is completed, and sometimes in the middle of the procedure, the bladder must be irrigated and cleared completely of any prostatic chips or clots. It would, however, facilitate the operation if irrigation fluid and the prostatic chips or clots could be removed without having to irrigate the bladder.

In the diathermy unit previously discussed, electricity is used both for cutting and coagulation. The electricity runs through a hot metal were (isolated in the proximal part) to cut pieces or chips of the prostate and to coagulate any bleeding areas. The use of these electrically operated resectoscopes has certain disadvantages. For example, there is a need for a very powerful diathermy machine; the electric loops through which the electricity runs have an average useful life of only one or two patients; each loop costs approximately fifty dollars; and the procedure produces tissue charring or carbonization which produces a slightly higher risk of a location for infection. (Charred tissued is dead tissue and with urine and blood flows close thereto, bacteria might find a suitable place to multiply.)

Furthermore, while operating time depends greatly on the size of the prostate as well as the skill of the operator, other considerations also increase operating time. These include excessive bleeding and a small bladder capacity to receive the irrigation fluid and the removal of prostatic chips. The average skilled operator or surgeon may take approximately one minuite to remove each gram of prostatic tissue. Since the majority of prostate surgical removals are under 100 grams, e.g., approximately 20 to 60 grams, it can be seen that the process can become quite time consuming—and there are some prostates that range in size from 100 to 250 grams. Accordingly, it can be seen that any process or apparatus which might decrease the operating time would be very beneficial.

It is known that lasers can be very useful in surgical applications, but there has never been an acceptable application of laser surgery apparatus or techniques to prostate resections. Since precision cutting and the ability to control the laser beam to control bleeding are two major benefits of the use of lasers in surgery, and since these are two of the most important considerations during prostate resections, it would be very beneficial if an apparatus were available which provides the benefits of laser technology for prostate surgery.

A further consideration of prostate surgery is the fact that the capsule of the prostate contains many veins, and if any of these are breached, the capsule will bleed profusively and will allow the irrigation fluid to escape outside the urinary system into the area surrounding the prostate. This not only causes pain, but electrolyte disturbance with an increased morbidity and even possibly mortality. In order to avoid piercing the capsule, many resectionists stop short of the capsule by 0.5-1 mms or more depending on the skill of the operator and anatomy of the prostate. It would, of course, be benefical to get as close to the capsule as possible in removing the prostate tissue, but it takes a highly skilled resectionist to come this close without invading the capsule. Such skill is only obtained after many years of practice.

In this regard, it would be very helpful if a method could be provided whereby surgeons could perform prostate surgery knowing when they are getting close to the capsule. Having such knowledge of the progress during the resectioning would allow much more thorough removal of the undesireable tissue and at the same time reduce the anxieties associated with possible invasion of the capsule.

OBJECTS OF THE INVENTION

It is an object of this invention to increase the speed and efficiency and decrease the cost of the cutting operation associated with transurethral surgery of the prostate gland and/or bladder and provide for a safer operation.

It is a further object of this invention to provide a resectoscope which provides irrigation fluid directly to the situs of the cutting and at the same time withdraws the irrigation fluid and the chips removed from the prostate through the resectoscope without the need to irrigate the bladder.

It is another object of this invention to provide a laser for use in conjunction with prostate or bladder surgery in order to enhance the accuracy and speed of cutting and also to coagulate tissue in order to stop or minimize bleeding.

It is yet another object of the invention to provide a rotatable cutting member which can be automatically or manually operated for prostate resections.

It is also an object of the invention to provide an apparatus and method wherein a resectoscope utilizing a laser as a cutting member has the laser controlled by a computer operated in conjunction with ultrasound in order to prevent unintentional cutting of the prostate beyond the central zone where the transurethral resectioning is to occur.

SUMMARY OF THE INVENTION

The above and other objects of the invention are achieved by providing a resectoscope having a rotating cutting element mounted within an outer sheath adapted to be inserted in to the urethra. The cutting element has helical threads along the length thereof and a cutting blade at the distal end. The outer sheath has a covered distal end portion which extends beyond and over the cutting blade and has an opening therethrough adjacent the cutting blade. Spaced from and within the outer sheath is an inner sheath surrounding the cutting element. The inner sheath has a length less than the cutting element so that the cutting blade at the end of the cutting element is exposed within the outer sheath. An optic fiber for transmission of a laser light (e.g., N.D. YAG laser) or a metal conduit for transmission of the laser light (e.g., a C02 laser) is positioned within the space between the inner and outer sheaths and extends along the length of the inner sheath to a position adjacent the cutting blade. The optic fiber or metal conduit is adapted to be moved by the rotation of the cutting element so that the laser light beam advances through tissue to cut and coagulate the resected area before the cutting blade of the cutting element reaches the resected tissue.

The space between the inner and outer sheaths is adapted to receive irrigation fluid at the proximal end of the outer sheath so that the irrigation fluid flows toward the distal end of the sheaths to the location of the cutting blade in order to irrigate the resected area. The irrigation fluid is withdrawn through the inner sheath by a vacuum communicating with the inner sheath and also by the influence of the helical threading surrounding the cutting element which directs the irrigation fluid and chips of the resected tissue rearward through the inner sheath to an outlet at the proximal end of the inner sheath.

A telescope is provided through the cutting element for viewing the area being resected, and automatic and manual drive mechanisms are connected to the cutting element to provide continuous or selective rotation of the cutting element.

Additionally, a computer is provided so that a computer generated image of the prostate can be prepared by means of ultrasound, for example by inserting ultrasound probes into the rectum of the patient adjacent the prostate or by using exterior abdominal probe. This computer generated image is used to plot the area of the prostate to be resected, and by connecting the computer to the laser and to an ultrasound probe, the cutting of the prostate tissue can be followed by the ultrasound probe and this information fed into the computer. By comparing the location of the resectoscope to the original ultrasound plot of the prostate, the cutting can be contained within limited areas by having the computer shut off the laser when comparison indicates that the wrong areas are about to be cut.

BRIEF DESCRIPTION OF THE DRAWINGS

Other objects and many of the attendant advantages of this invention will be readily appreciated as the same become better understood by reference to the following detailed description when considered in conjunction with the accompanying drawings, wherein:

FIG. 1 is a side view of the resectoscope of the present invention;

FIG. 2B is an enlarged, partial section view of the distal end of the resectoscope of the present invention;

FIG. 3 is a section view taken along the line 3—3 of FIG. 2A;

FIG. 4 is an enlarged section view taken along the line 4—4 of FIG. 2B;

DESCRIPTION OF THE PREFERRED EMBODIMENT OF THE INVENTION

Figure 2A:
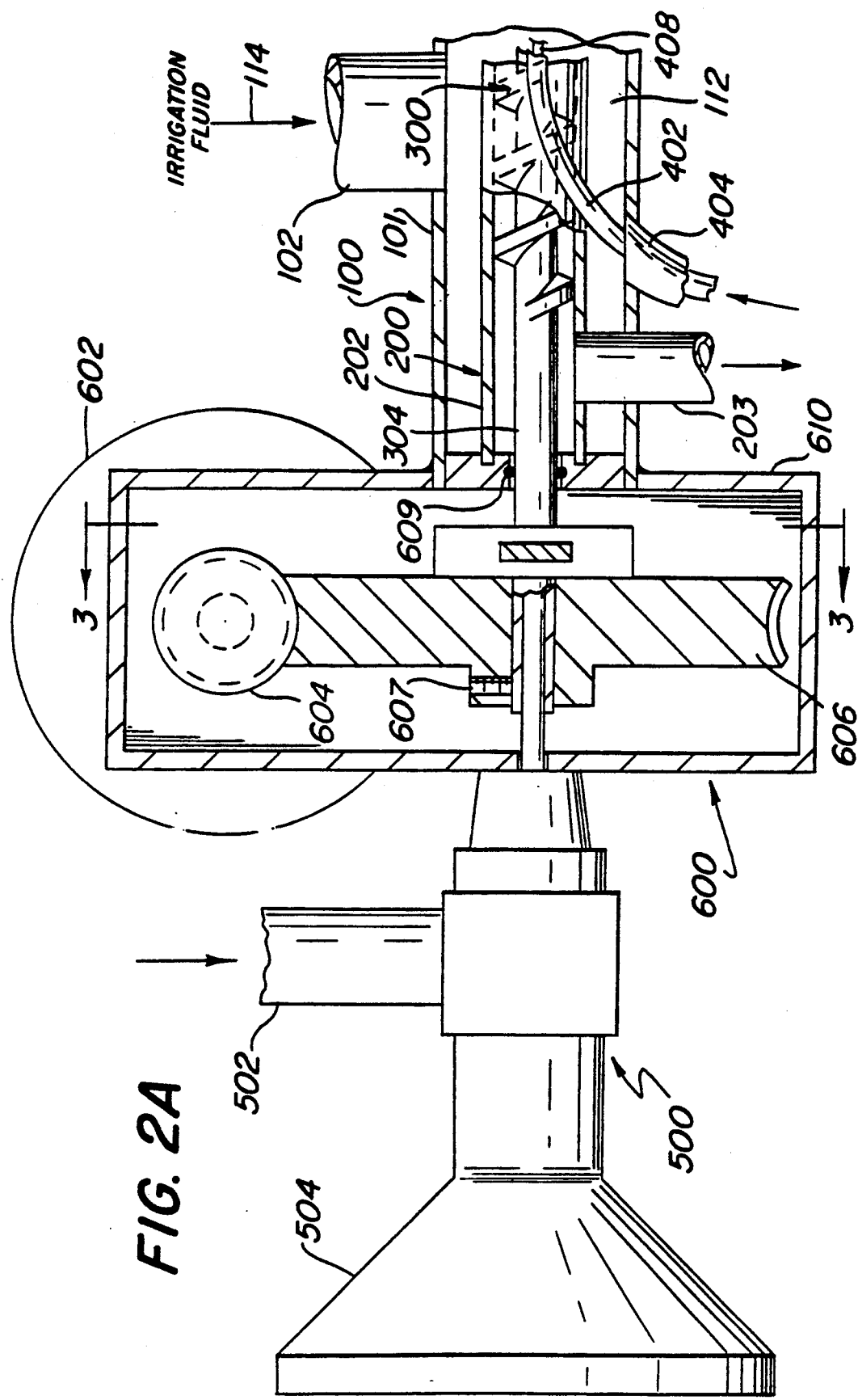
FIG. 2A is an enlarged, partial section view of the drive mechanism and proximal end of the resectoscope of the present invention.

Referring in greater detail to the various figures of the drawings wherein like reference characters refer to like parts, a resectoscope of the present invention is generally shown at 10 in FIG. 1.

The resectoscope 10 includes a tubular outer sheath 100 adapted to be inserted into the urethra for the purpose of performing either prostate or bladder surgery, as is well known in the art. Specifically the outer sheath is inserted into the urethra to prevent it from collapsing while the operating procedure is carried out utilizing the working elements housed within the sheath 100.

As shown in FIG. 2B, within and spaced from the outer sheath 100 is a second or inner tubular sheath 200, housing therein a cutting element 300. The cutting element 300 is adapted to rotate within the inner sheath 200. In the space between the outer sheath 100 and the inner sheath 200 is a third sheath 402. This third sheath 402 is part of the laser member 400 of the resectoscope and houses therein an optic fiber filament 408 which transmits the laser light beam. This third sheath 402 is affixed (for example, by being welded) at one end to the inner sheath 200, and its free end is radially moveable within the space between the inner and outer sheaths when it is contacted by the cutting element 300.

The cutting element 300 has a longitudinal opening 302 along the longitudinal axis thereof through which fits a telescope 500 for use in viewing the area of the bladder or prostate being resected.

The cutting element 300 is connected to a drive mechanism 600 which may rotate the cutting element either continuously or intermittently. As will be described in more detail, the drive mechanism 600 is preferably pneumatically operated for continuous rotation of the cutting element 300 or manually operable for more careful rotation of the cutting element 300.

As shown in FIGS. 1 and 2A, the outer sheath 100 includes a hollow, preferably stainless steel, first tube 101 approximately eleven inches long. A conduit 102, which is designed for connection to a source of sterile irrigation fluid, is provided to introduce irrigation fluid into the resectoscope and ultimately to the area of the prostate being resected. A valve 104 in conduit 102 controls the flow of fluid into the first tube 101.

The distal end of the first tube 101 has a closed end or rounded hood 106 and an opening 108 on the underneath side of the tube 101. It is through this opening 108 that the cutting element 300 is exposed and is able to cut away at the tissue being removed. At the proximal end of the tube 101 opposite the hood 106 is a handle 110 perpendicular to the tube 101 which is used to manipulate or maneuver the resectoscope 10.

The inner sheath 200, as shown in FIGS. 2A and 2B, is a hollow open-ended second tube 202 narrower in outside diameter than the inside diameter of the first tube 101 and positioned within and longitudinally axially concentric with the first tube 101. A second conduit 203 is connected to the second tube 202 and passes through the first tube 101. This conduit 203 is designed to be connected to a vacuum source (not shown) and has a control valve 206 (FIG. 1) associated therewith for controlling fluid flow out of the interior of the second tube 202. The location where the second conduit 203 passes through the first tube 101 is sealed so there is no possibility of leakage.

Figure 5:
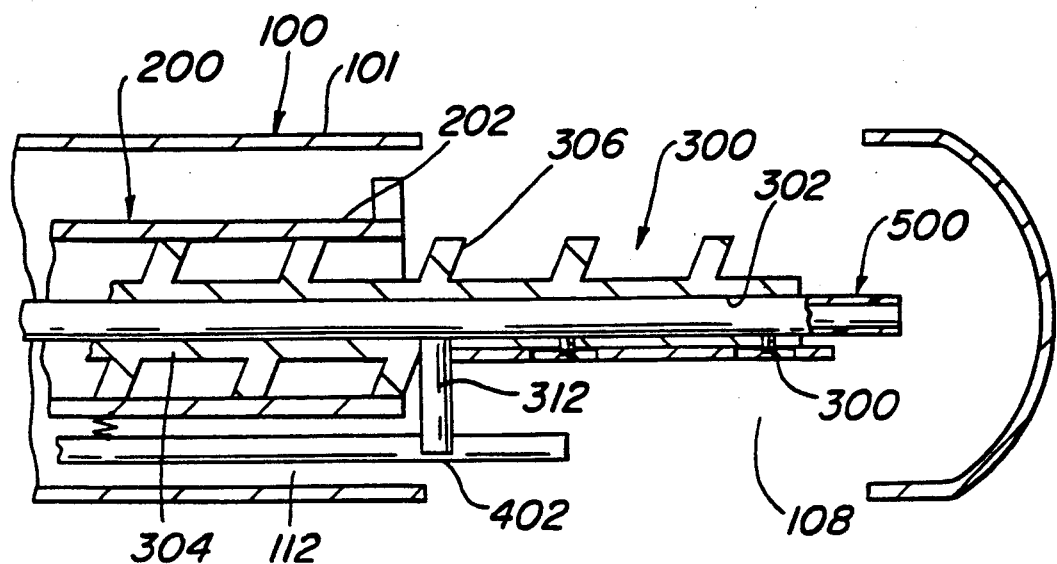
FIG. 5 is an enlarged section veiw taken along the line 5—5 of FIG. 2B.

Within the second tube 202 is the rotatable cutting element 300. As shown in FIGS. 2B and 5, the cutting element includes a hollow tube 304 surrounded by a continuous helix or threads 306 about the circumference thereof. These threads 306 run from the distal end of the hollow tube 304 along the length thereof, but stop short of conduit 203 connected to the vacuum source through which the irrigation fluid and removed tissue are withdrawn from the resectoscope. The longitudinal axis of the hollow tube 304 is coaxially aligned with the first and second tubes, 101 and 202. At the distal end of the hollow tube 304 is a curved blade 306 for cutting and removing the desired tissue. The distal end of the hollow tube 304 extends beyond the distal end of the second tube 202.

In the preferred embodiment, the blade 306 is made of stainless steel and affixed to the end of the hollow tube 304 by screws 308a, 308b which pass through the blade 306 and into the tube 304. The blade 306 is, thus, removeable or replaceable. The screws 308a, 308b are preferably flush with the surface of the blade 306. As shown in FIG. 4, the blade 306 is curved. This allows the blade to "scoop" away the resected tissue.

The hollow tube 304 also has extending therefrom at the distal end thereof, but before the cutting blade 306 a first projection 312 (FIG. 4) which projects outwardly or radially away from the hollow tube 304 and beyond the helical threads 305. The first projection plays an important role in movement of the laser 400, as will be discussed later.

The opening 302 extends completely longitudinally through the hollow tube 304, and the longitudinal axis of the opening 302 is concentric with the longitudinal axes of the first and second tubes 101, 202. The opening 302 through the hollow tube 304 is designed to receive and house the telescope 500 therein. The telescope 500 is of conventional construction and includes a connection 502 for a light source and has an eyepiece 504 for use in reviewing the area of the prostate gland or bladder to be cut with the resectoscope 10. The use of such a telescope in such a manner is known in the art.

The drive mechanism 600 is preferably a pneumatic-type system 602 such as that known in the medical art to run drills, e.g. a dentist's pneumatic drill. While shown in simplified form in FIGS. 2A and 3, the specific construction and connection of such a drive system 602 to the rod 304 in order to rotate the rod are well known to those skilled in the art and are not presented in detail herein. However, as shown in FIGS. 2A and 3, a pneumatic drive 602 rotates a threaded shaft 604 which in turn causes gear wheel 606 to rotate. The rod 304 is secured to the gear wheel 606 by a screw 607. A seal 609 prevents irrigation fluid from entering into the drive housing 610. It is preferred that the speed of the rotation of the rod 304 be controllable by means of a foot pedal (not shown) which regulates the flow of high pressure air to the drive system 602. It should be understood that while a pneumatic drive is preferred, other means of rotating the hollow tube, such as by different types of electrical motors might also be used. The drive mechanism is not intended to be limited to any specific form. A pnuematic drive mechanism is preferred because it is more easily cleaned and sterilized.

To more accurately control the rotation of the rod 304 and the cutting of the blade 306 attached thereto, an additional hand-operable pawl and ratchet-type drive mechanism 608 (FIG. 3) may be provided in order to rotate the rod 304 independent of the rotation imparted by the pneumatic drive 602. A pawl and ratchet drive 608 is not considered to be unique and construction of such a means for continuously, yet manually, rotating the rod 304 is well known to those skilled in the art and is not discussed at length herein. An example of such a type of mechanism is the type of mechanism used in a manual rapid photographic film advance system.

As shown in FIG. 2A, passing through the first tube 101 at the rearward or proximal portion of the tube 101 is the laser member 400. The laser member 400 includes an inlet tube 404 which passes through the first tube 101 and communicates with the third sheath or tube 402. The third tube passes longitudinally through the space 112 between the first and second tubes 101, 202 toward the end of the hollow tube 304 having the cutting blade 306 thereon. The third tube 402 is preferably made of resilient stainless steel and is affixed, for example by a weld, at its proximal end to the second tube 202. In this manner, the rearward or proximal end of the third tube 402 is stationarily positioned in relation to the second tube 202. The opposite or distal end of the third tube 402, the end adjacent the blade 306, however, is free to move through a limited radial arc. The distal end of the third tube 402 extends in front of the first projection 312 on the hollow tube so that the first projection 312 abuts the third tube 402 as the hollow tube 304 rotates and thereby forces the third tube 402 ahead to move in the direction of rotation of the rod 304.

To prevent the third tube 402 from wrapping around the second tube 202, a special configuration is provided on the second tube 202 as shown in FIG. 4. The second tube 202 has at least near the distal end thereof a second projection or cam 208 which gradually projects outward radially from the circumference of the second tube 202 a distance greater than the distance which the first projection 312 extends beyond the general circumference of the second tube 202. When the third tube 402 (which usually lies adjacent to the second tube 202) is engaged by the first projection 312 as the hollow tube 304 rotates, the third tube 402 moves around the second tube 202 under the force exerted by the first projection 312 and advances upward along the cam 208 as shown by the phantom lines in FIG. 4. When the third tube 402 is atop the second projection 208 at the position farthest away from the general circumference of the second tube, the third tube is spaced so far radially from the second tube that the first projection 312 passes underneath the third tube 402 and no longer causes the third tube to move radially about the second tube 202.

A spring 406 is attached between the third tube 402 and second tube 202 near the free end of the third tube so that the third tube is urged back toward the second tube after it reaches the top of the second projection 208 and clears the head of the first projection 312. The purpose of the spring 406 is to return the third tube 402 to its initial position as quickly as possible so that the third tube is in position to be engaged by the first projection 312 when it begins the next cycle of rotation. Although a coiled spring 406 is shown, any suitable biasing device may be used. In this manner, as the hollow tube 304 passes through each complete rotation, the first projection 312 abuts the third tube and urges it forward in front of the blade 306 until the third tube rides to the top of the cam 208. When the third tube 402 clears the first projection 312, it is pulled back to its position adjacent the second tube 202 under the urging of the biasing spring 406.

The purpose of the third tube 402 is to provide a sheath for the optic fiber filament 408 to pass therethrough. The filament 408 is inserted through a resilient gasket-type fitting 410 (FIG. 1) (which fits tightly around the filament 408), through the inlet tube 404 and onward toward the open distal end of the third tube 402. As the third tube moves along the cam 208, the laser light beam projected from the end of the optic fiber filament 408 is directed outward from the third tube 402 in front of and parallel to the cutting edge 310 of the blade 306. The optic filament, of course, reciprocates back and forth with the motion of the third tube.

The hood 106 of the first tube 101 is positioned in front of the optic fiber filament 408 in such a manner that the laser beam from the filament does no forward laser cutting of tissue. The hood 106 stops or absorbs the forward laser light from the optic fiber filament. The only cutting by the laser light is along the line parallel to the cutting edge 310 of the blade 306.

The proximal end of the optic filament 408 is connected to a laser generator 412 which is provided with a foot control. As an example, a KTP/532 Laser by Laserscope of Santa Clara, Calif. is a suitable type of optic fiber laser system. The optic fiber filament 408 is typically a 400 u optic laser cable.

The laser, when energized, assists in cutting and also assists in coagulating the tissue to stop or minimize bleeding. Preferably, the optic fiber filament 408 is attached to a laser generator at approximately 532 nm with a power of 5–15 watts pulsed at 0.10–0.5 seconds. A foot pedal is used to energize the laser. At times during the resection procedure, the distance of the optic fiber filament 408 to the target tissue may need to be adjusted in order to control cutting or coagulation (as known in the art.) The distance is regulated simply by manually pushing or pulling the filament 408 through the gasket 410. The gasket 410 holds the filament sufficiently tightly so that once manipulation of the filament is complete, the filaments stays tightly at the selected location within the third tube 402.

In order to perform the resection of the prostate, the resectoscope 10 is inserted through the urethra toward the prostate and the area where resection is desired. Irrigation fluid 114 is provided through the conduit 102 and valve 104 to the inside of the first tube 101. The fluid flows within the space 112 between the first and second tubes toward the hood 106 portion of the first tube. The irrigation fluid serves to irrigate and clear the area being resected, and in order to keep the area clear, the fluid is removed from the cutting area through the second tube 202 by being drawn through the conduit 203 through valve 204 which is connected to the vacuum source. While the vacuum tends to withdraw the irrigation fluid and resected chips, the rotation of the hollow tube 304 with the threads 305 therearound also causes fluid flow in the direction of the outlet conduit 203.

Upon engaging the drive mechanism 600, the hollow tube 304 rotates the blade 306 at the end thereof. The first projection 312 (as discussed previously) contacts the third tube 402 and begins to advance the third tube and the optic filament 408 within the third tube. The laser is activated in the required manner, and the laser light beam projecting from the optic filament within the third tube is directed in a path parallel to and in front of the cutting edge 310 of the blade 306 to provide a cutting and coagulating function.

In order to view the process of the cutting, the operator views the cutting location through the telescope 500 which is inserted through the opening 302 in the rod 304. Preferably, the telescope is a 30 degree telescope and has a light source connected thereto at connection 502. By providing this telescopic vision, the entire procedure can be done visually.

As has been explained previously, rotation of the rod 304 is produced and controlled preferably by a pneumatic drive system 602, and movement of the rod 304 causes movement of the third tube 402 containing the filament 408 in advance thereof. If more precise cutting is necessary, movement of the hollow tube 304 can be controlled manually by the manual system 608. In addition to manually controlling the motion of the hollow tube 304 and the laser light in front of the blade, this manual control can also be used to direct the optic fiber filament toward any particular area which may be bleeding and needs to be coagulated since the optic fiber moves along with the tube 402 when it is contacted by the projection 312 on the hollow tube 304.

Figure 6:
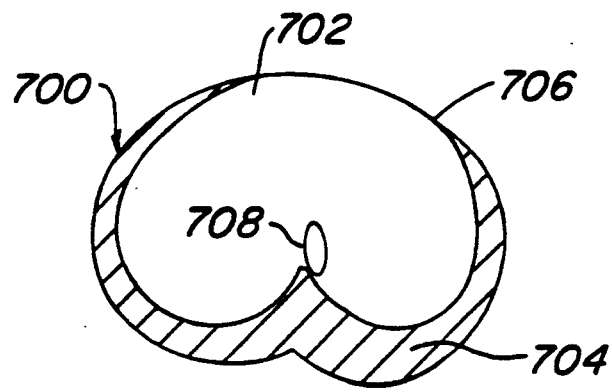
FIG. 6 is a transverse section of the prostate.

In a further embodiment of the invention, the laser resectoscope 10 of the invention is operated in conjunction with a computer 800 in order to control cutting by the resectoscope 10 and thereby prevent the unintentional breaching of the prostate capsule or the peripheral zone during prostate surgery. As shown in FIG. 6 the prostate 700 comprises a central zone 702 surrounded by a peripheral zone 704 and capsule 706 surrounding the urethra 708. Only the central zone 702 is removed during transurethral prostate resectioning, and in particular, the capsule 706 and peripheral zone 704 are not to be breached during the surgery.

To have a better idea of the size of the prostate being resectioned and the location of the boundaries of the central zone 702 prior to commencing the prostate surgery, by using known ultrasound technology, ultrasound probes can be used to measure and diagram, with the assistance of a computer 800 connected to the probe(s), the shape of the prostate 700. For example, by using either a rectal probe or an abdominal probe (such as produced by Bruel & Kjaer of Denmark), a three dimensional scan is made of the prostate by feeding the ultrasound scans into a computer 800 where an image is prepared showing the central zone of the prostate in addition to the capsule and the peritheral zone.

The image boundaries of these specific locations within the prostate are retained in the computer so that the computer can be instructed which areas of tissue are to be removed and therefore, which regions of the prostate the laser cannot be allowed to penetrate.

The use of ultrasound probes is known in the art to permit computer imaging of the prostate. However, it is not known in the art to connect the computer 800 (wherein the image is stored) to a resectoscope 10 in order to control the cutting operation of the resectoscope, and in particular such a connection is not known with a resectoscope utilizing a laser light for cutting. If, during the resecting process the laser light begins to come within an unacceptably close range of the edge of the capsule 706 or the peripheral zone 704, so that there is a possibility of breaching the capsule or peripheral zone, the computer 800 in conjunction with ultrasound probing detects the nearness of the laser or cutting blade to the capsule or peripheral zone and will automatically direct the shut off of the laser generator. In this way, inadvertant resection of the capsule or peripheral zone is avoided.

The ultrasound probing need not be continuous throughout the entire operation; however, during at least that part of the resection where the surgeon feels the resectoscope is getting close to the capsule or the peritheral zone, the ultrasound can again be applied to the prostate area to follow the location of the resectoscope 10. By comparing the location of the resectoscope 10 to the previously generated image of the prostate 700, the computer 800 can be used to detect when the laser resectoscope scope is getting too close to an area which should not be penetrated and turn off the laser. The computer 800 is used to only control the operation of the laser. Neither the light source nor the ultrasound activity is affected by the computer.

It is recognized that as skills in the use of computers and ultrasound increase, additional methods of computing or determining the location of the resectoscope within the central zone may be developed. These future advances in technology are, however, considered to be within the realm of the computer-assisted technique disclosed herein.

Without further elaboration, the foregoing will so fully illustrate my invention that others may, by applying current or future knowledge, readily adopt the same for use under various conditions of service.

What is claimed as the invention is:

1. A surgical apparatus for coagulating tissue of the prostate of a living being, said apparatus comprising:
    elongated introduction means configured for introduction through the urethra into said being, said introduction means being positionable adjacent said prostate within said being;
    laser means associated within said introduction means and configured for introduction by said introduction means to a location within said urethra adjacent said prostate, said laser means being controllable for producing and directing a laser beam through said urethra into said prostate tissue adjacent said introduction means for coagulating said prostate tissue;
    ultrasonic imaging means coupled to said laser means for introduction into the body of said being adjacent said prostate to provide an image of at least a portion of said prostate tissue as said laser means is operated to enable said laser means to be controlled to coagulate said adjacent prostate tissue while precluding injury to other adjacent tissue; and
    tissue removal means for removing at least a portion of said coagulated prostate tissue from said prostate.

2. A surgical apparatus as claimed in claim 1, wherein:
    said introduction means has a distal end portion and said distal end portion is positionable adjacent said prostate tissue;
    said laser beam is provided at said distal end of said introduction means.

3. The apparatus of claim 1 wherein said tissue removal means is arranged to operate substantially contemporaneously with the operation of said laser.

4. The apparatus of claim 3 wherein said tissue removal means comprises means for carrying said removed coagulated prostate tissue out of the body of said being.

5. The apparatus of claim 4 wherein said tissue removal means additionally comprises cutting means.

6. The apparatus of claim 5 wherein said cutting means is arranged to be rotated about an axis.

7. The apparatus of claim 4 wherein said means for carrying said removed coagulated tissue comprises suction means.

8. The apparatus of claim 1 wherein said tissue removal means comprises cutting means.

9. The apparatus of claim 8 wherein said cutting means is arranged to be rotated about an axis.

10. A method of coagulating tissue of the prostate of a living being, said method comprising the steps of:
    introducing elongated means through the urethra into the body of said being to a position adjacent said prostate, said elongated means having controllable laser means therein for providing a laser beam;
    operating said laser means in order to produce a laser beam and directing said laser beam through said urethra into said prostate tissue adjacent said elongated means in order to coagulate said prostate tissue;
    utilizing ultrasonic imaging means coupled to said laser means and inserted into the body of said being to a location adjacent said prostate to provide an image of at least a portion of said prostate tissue as said laser means is operated to enable said laser means to be controlled to coagulate said adjacent prostate tissue while precluding injury to other adjacent tissue.

11. The method as claimed in claim 10 wherein:
    said elongated means has a distal end portion, and wherein said method additionally comprises introducing said distal end portion to a position adjacent said prostate tissue; and wherein
    said laser beam emanates from said distal end portion of said elongated means.

12. The method of claim 10 additionally comprising the step of removing at least a portion of said coagulated prostate tissue from the body of said being.

13. The method of claim 12 wherein said coagulated prostate tissue is removed from the body of said being substantially contemporaneously with the operation of said laser means.

14. The method of claim 12 additionally comprising the step of carrying said coagulated prostate tissue out of the body of said being.

15. The method of claim 12 wherein said coagulated prostate tissue is cut from said prostate.

16. The method of claim 15 wherein said cutting is accomplished by a rotatable cutter.

17. The method of claim 15 wherein coagulated tissue is removed from the body of said being by suction.

18. The method of claim 12 wherein coagulated tissue is removed from the body of said being by suction.

* * * * *